US007358270B2

(12) United States Patent
Nishida et al.

(10) Patent No.: US 7,358,270 B2
(45) Date of Patent: Apr. 15, 2008

(54) TREATING AGENT FOR IRRITABLE BOWEL SYNDROME

(75) Inventors: Akito Nishida, Tokyo (JP); Akira Niwa, Tokyo (JP); Yutaka Atsuta, Tokyo (JP)

(73) Assignee: Astellas Pharma Inc., Tokyo (JP)

(*) Notice: Subject to any disclaimer, the term of this patent is extended or adjusted under 35 U.S.C. 154(b) by 54 days.

(21) Appl. No.: 11/047,142

(22) Filed: Jan. 28, 2005

(65) Prior Publication Data
US 2005/0192329 A1 Sep. 1, 2005

Related U.S. Application Data

(63) Continuation-in-part of application No. PCT/JP2004/006657, filed on May 12, 2004, which is a continuation-in-part of application No. PCT/JP2004/000896, filed on Jan. 30, 2004.

(51) Int. Cl.
*A61K 31/4184* (2006.01)
*A61K 31/404* (2006.01)

(52) U.S. Cl. .................................................. 514/394

(58) Field of Classification Search ................ None
See application file for complete search history.

(56) References Cited

U.S. PATENT DOCUMENTS

| | | | |
|---|---|---|---|
| 4,067,974 | A | 1/1978 | Sasmor |
| 5,223,508 | A | 6/1993 | Izawa et al. |
| 5,344,927 | A | 9/1994 | Ohta et al. |
| 2002/0040033 | A1 | 4/2002 | Cautreels et al. |
| 2002/0150624 | A1 | 10/2002 | Watanabe et al. |
| 2003/0143548 | A1 | 7/2003 | Camilleri et al. |
| 2005/0026981 | A1 | 2/2005 | Sugihara et al. |

FOREIGN PATENT DOCUMENTS

| | | |
|---|---|---|
| EP | 0 274 845 | 7/1988 |
| EP | 1 205 190 A1 | 5/2002 |
| JP | 5-6226 | 3/1999 |
| WO | WO 99/17755 | 4/1999 |

OTHER PUBLICATIONS

The Merck Manusal, 17th edition (1999), p. 312.*
M. Ohta et al., Chem. Pharm. Bull., 44(5):991-999 (1996).
M. Ohta et al., Chem. Pharm. Bull., 44(5):1000-1008 (1996).
M. Ohta et al., Chem. Pharm. Bull., 44(9):1707-1716 (1996).
M. Ohta et al., Chem. Pharm. Bull., 44(9):1717-1722 (1996).
K. Miyata et al., Journal of Pharmacology and Experimental Therapeutics, 261(1):297-303 (1992).
K. Miyata et al., American Physiological Society, pp. G827-G831 (1998).
T. Hirata et al., Pharmacology Laboratories, Institute for Drug Discovery Research, Yamanouchi Pharmaceutical Co., Ltd., pp. 1-6 (2003) (including English language translation).
Japanese Pharmaceutical Excipients Dictionary, First Edition, complied by Japan Pharmaceutical Excipients Council and published by Yakuji Nippo, Ltd. (Jan. 14, 1994), p. 2, "Ascorbic Acid" section; p. 3, "L-Aspartic Acid" section; p. 18 "Erythorbic Acid" section; pp. 38 to 39, "Citric Acid" section; p. 65, "Tartaric Acid" section; p. 113, "Fumaric Acid" section; p. 117, "Propyl Gallate" section.
K. Masaki et al., Kagakurycho no Ryoiki, 14(11):2004-2008 (1998).
T. Kuwabara et al., J. Gastroenterol., 29:721-726 (1994).
N. Kishibayashi et al., J. Med. Chem., 36:3286-3292 (1993).
Japan Pharmaceutical Reference, The Fifth Edition (1999), Nasea Injection 0.3 mg (p. 1278-1280) and Nasea OD Tablets 0.1 mg (p. 1281-1283).
Ramosetron hydrochloride, Drugs of the Future, vol. 21, No. 1, 1996, 116-116.
A. Ozaki et al. Effect of the 5-hydroxytryptamine$_3$ (5-ht$_3$)-receptor antagonist KB-R6933 on experimental diarrhea models, Jpn. J. Pharmacol., vol. 80, 1999, 93-96, XP009047033.
H. Ito, et al. Investigation of the effects of YM-31636, a novel 5-ht$_3$ receptor agonist, on defecation in normal and constipated ferrets, European Journal of Pharmacology, vol. 424, 2001, 151-157.
C. Steadman et al. Selective 5-Hydroxytryptamine Type 3 Receptor Antagonism with Ondansetron as Treatment for Diarrhea-Predominant Irritable Bowel Syndrome: A Pilot Study, Mayo Clinic Proceedings, Mayo Medical Ventures, Rochester, MN, US, vol. 67, No. 8, Aug. 1992, 732-738, XP002098638.
G. Stacher et al. Effects of the 5-HT$_3$ Antagonist Cilansetron vs Placebo on Phasic Sigmoid Colonic Motility in Healthy Man: a Double-Blind Crossover Trial, British Journal of Clinical Pharmacology, Blackwell Scientific Publ, GB, vol. 49, No. 5, 2000, 429-436.
T. Hirata et al., Usefulness of 5-HT3 receptor antagonists in irritable bowel syndrome—pharmacological profile of ramosetron hydrochloride, Saibo, 2003, vol. 35, No. 10, p. 398-401.
Kikuta et al., Japanese Journal of Pediatrics, 52:425-432 (1999).
Noda et al., Japanese Journal of Clinical and Experimental Medicine, 71(10):2753-2764 (1994).
Nakajima et al., The Japanese Journal of Clinical and Experimental Medicine, 71(9):2461-2468 (1994).
Sekino et al., Japanese Pharmacology and Therapeutics, 22(9):3877-3888 (1994).
Noda et al., The Japanese Journal of Clinical and Experimental Medicine, 71(10):2765-2776 (1994).
Noda et al., Journal of New Remedies & Clinics, 43(11):2241-2255 (1994).
Taketani et al., The World of Obstetrics and Gynecology, 46(12):965-973 (1994).
Taketani et al., Obstetrics & Gynecology, 61(12):1759-1770 (1994).
Kawabata et al., Nishinihon Journal of Urology, 56:1445-1456 (1994).
Mori et al., The Journal of Adult Diseases, 24(12):2257-2265 (1994).
Sato et al., Japan Journal of Cancer Clinics, 50(4):305-313 (2004).
Noda et al., Journal of New Remedies & Clinics, 45(7):1309-1321 (1996).
Noda et al., Journal of New Remedies & Clinics, 45(3):482-490 (1996).
Taketani et al., Obstetrics & Gynecology, 63(9):1297-1308 (1996).
Taketani et al., The World of Obstetrics and Gynecology, 48(8):749-760 (1996).
Noda et al., Journal of New Remedies & Clinics, 45(8):1445-1462 (1996).

* cited by examiner

*Primary Examiner*—Phyllis G. Spivack
(74) *Attorney, Agent, or Firm*—Peter F. Corless; Edwards Angell Palmer & Dodge LLP

(57) ABSTRACT

A therapeutic method and pharmaceutical compositions for treatment of irritable bowel syndrome including non-constipated irritable bowel syndrome such as diarrhea-predominant irritable bowel syndrome and alternating constipation/diarrhea irritable bowel syndrome in male and female patients, which may comprise administering a patient with from 0.001 to 0.05 mg of ramosetron hydrochloride as a daily dose or an equivalent molar amount of ramosetron or its pharmaceutically acceptable other salt.

24 Claims, No Drawings

1

TREATING AGENT FOR IRRITABLE BOWEL SYNDROME

This application is a continuation-in-part of International Application No. PCT/JP04/000896 filed Jan. 30, 2004 which designated the United States and International Application No. PCT/JP04/006657 filed May 12, 2004 which also designated the United States, both of which applications are incorporated herein by reference in their entirety.

TECHNICAL FIELD

The present invention relates to a drug or, more particularly, to a treating agent for irritable bowel syndrome including non-constipated irritable bowel syndrome such as diarrhea-predominant irritable bowel syndrome as well as an agent for improving the symptom of diarrhea of irritable bowel syndrome.

BACKGROUND ART

Ramosetron is called (−)-(R)-5-[(1-methyl-1H-indol-3-yl)carbonyl]-4,5,6,7-tetrahydro-1H-benzimidazolein its chemical name.

Ramosetron hydrochloride has been sold as an agent for improving the gastrointestinal symptoms (nausea and vomiting) associated with anticancer drug therapy (such as cisplatin) and it is usually administered to adults either orally at 0.1 mg once daily or intravenously at 0.3 mg once daily ("Nasea OD Tablet 0.1 mg", "Nasea Injections 0.3 mg" in JAPAN PHARMACEUTICAL REFERENCE, PRODUCTS and ADMINISTRATION in JAPAN, The Fifth Edition (1999) published by the Japan Medical Products International Trade Association).

In EP-A-381422, there is a disclosure that a series of tetrahydrobenzimidazole derivatives including ramosetron and pharmaceutically acceptable salts thereof has an antagonistic action to $5HT_3$ receptors. On the basis of such an action, there is suggested a possibility of suppression of emesis caused by anti-cancer drugs such as cisplatin and radioactive ray and prevention and treatment of migraine, complex headache, trigeminal neuralgia, anxiety symptom, gastrointestinal motility abnormalities, peptic ulcer, irritable bowel syndrome, etc. and there is a description that usual clinical dose per day for adults is 0.1 to 10 mg by intravenous injection and 0.5 to 50 mg by oral administration which is administered once daily or by dividing into several times.

On the other hand, in WO 99/17755, there is a description that $5HT_3$ receptors are useful for the treatment of female patients suffering from non-constipated irritable bowel syndrome and that the therapeutically effective dose is within a range of 0.01 to 500 mg or, preferably, 0.05 to 50 mg per day. To be more specific, as a result of clinical study where 1 to 8 mg of alosetron were administered twice daily to the patients suffering from non-constipated irritable bowel syndrome, significant improvement was noted in female patients as compared with placebo in relief of pain and discomfort, stool consistency, bowel movement frequency and the proportion of days with urgency treatment while, in male patients, no significant improvement was noted as compared with placebo except stool consistency.

In addition, in WO 2002/007713, there is a description that, when 1 to 16 mg of $5HT_3$ receptor antagonist are administered three times a day, that is useful for the treatment of irritable bowel syndrome in both male and female patients.

DISCLOSURE OF THE INVENTION

The present inventors have carried out intensive investigations for the purpose of creation of novel treating agents for irritable bowel syndrome including non-constipated irritable bowel syndrome such as diarrhea-predominant irritable bowel syndrome and alternating constipation/diarrhea irritable bowel syndrome for which no sufficiently effective treating agent has been available. The present inventors formerly tried clinical studies where ramosetron hydrochloride was administered twice daily to patients suffering from irritable bowel syndrome but significant therapeutic effect as compared with placebo was unable to be confirmed.

After that, the present inventors had the idea that the therapeutically effective dose of ramosetron to treat irritable bowel syndrome might be far lower than 0.1 to 0.3 mg which is a currently adopted dose as an improving agent for the gastrointestinal symptoms associated with anticancer drug therapy. In view of the above, a stable preparation containing very small amount (0.001 to 0.01 mg) of ramosetron hydrochloride was developed and clinical study using such a preparation was carried out for 12 weeks to male and female patients suffering from diarrhea-predominant irritable bowel syndrome. As a result, a remarkable efficacy has been surprisingly confirmed whereupon the present invention has been achieved.

Thus, the present invention relates to the therapeutic method of irritable bowel syndrome including non-constipated irritable bowel syndrome such as diarrhea-predominant irritable bowel syndrome and alternating constipation/diarrhea irritable bowel syndrome in male and female patients, including administering a patient with from 0.001 to 6 0.05 mg of ramosetron hydrochloride as a daily dose or an equivalent molar amount of ramosetron or its pharmaceutically acceptable other salt or it relates to the improving method of diarrhea symptom of irritable bowel syndrome in male and female patients, including administering a patient with from 0.001 to 0.05 mg of ramosetron hydrochloride as a daily dose or an equivalent molar amount of ramosetron or its pharmaceutically acceptable other salt.

In accordance with the present invention, it is now possible to provide an excellent agent for the treatment of irritable bowel syndrome including non-constipated irritable bowel syndrome such as diarrhea-predominant irritable bowel syndrome and alternating constipation/diarrhea irritable bowel syndrome or an agent for the improvement of diarrhea in irritable bowel syndrome of a diarrhea type for both male and female patients.

As shown in Test Example 1 which will be mentioned later, ramosetron hydrochloride was effective for patients suffering from diarrhea-predominant irritable bowel syndrome regardless of male and female by oral administration of 0.005 mg or 0.01 mg once daily. Since administration of 0.005 mg gave a significant therapeutic effect being the same as by administration of 0.01 mg, efficacy can be expected even by further one-half of that dose. Subjects of Test Example 1 are Japanese adult patients and there is suggested a possibility that the optimum dose for children will be smaller while it is often that the optimum dose for European and American people is twice as much of that of Japanese. Therefore, although the particularly preferred dose for ramosetron hydrochloride is within a range of 0.002 to 0.02 mg daily, it is likely that, depending upon the difference in age of the patient and among the races, a daily dose within a range of 0.001 to 0.05 mg is able to treat diarrhea-predominant irritable bowel syndrome or improve diarrhea symptom of irritable bowel syndrome.

Thus, more particularly, for certain human patient populations which may include Americans and Europeans for treatment of irritable bowel syndrome including diarrhea-predominant irritable bowel syndrome or to improve diarrhea symptom of irritable bowel syndrome, an optimum daily dose of ramosetron (amounts based on free base form) may be within a range of from 0.0025 mg to 0.05 mg, or even more suitably a daily dose within a range of from 0.0025 mg to 0.02 mg or equivalent molar amounts of a pharmaceutically acceptable salt of ramosetron. Thus, for instance, such a more suitable daily dosage range for ramosetron hydrochloride would be from 0.00283 mg to 0.0226 mg.

The invention also includes pharmaceutical compositions that contain 0.001 to 0.05 mg of ramosetron hydrochloride or an equivalent molar amount of ramosetron or other pharmaceutically acceptable salt thereof, and suitably contain 0.005 to 0.01 mg of ramosetron hydrochloride or an equivalent molar amount of ramosetron or other pharmaceutically acceptable salt, or 0.002 to 0.02 mg of ramosetron hydrochloride or an equivalent molar amount of ramosetron or other pharmaceutically acceptable salt. Also provided are pharmaceutical compositions that contain 0.0025 to 0.02 mg of ramosetron or an equivalent molar amount of a pharmaceutically acceptable salt of ramosetron. Pharmaceutical compositions of the invention may suitably further contain one or more pharmaceutically acceptable carriers. Preferred pharmaceutical compositions are formulated to provide the total daily dosage amounts of ramosetron or pharmaceutically acceptable salt thereof as disclosed herein in a single or multiple administration, e.g. oral dosage compositions (such as tablets, capsules, lozenges, etc.) that are formulated to provide the total daily dosage amount by daily administration to a patient of one or more such oral dosage forms.

In EP-A-381422, there is a description that a clinical dose of tetrahydrobenzimidazole derivative including ramosetron is usually 0.1 mg or more per day and there is neither suggestion nor disclosure that ramosetron hydrochloride shows a therapeutic effect by a daily dose within a range of 0.002 to 0.02 mg. In addition, the present invention is better:

1) than the improving agents containing ramosetron hydrochloride as an effective ingredient and being commercially available at present for the gastrointestinal symptoms associated with anticancer drug therapy in that the therapeutically effective dose is lower by as much as 1/5 to 1/50,
2) than the drugs disclosed in WO 99/17755 in that a sufficient therapeutic effect is achieved regardless of male and female patients and
3) than the drugs disclosed in WO 2002/007713 in that a sufficient therapeutic effect is achieved by administration of dose lower by as much as 1/50 to 1/500 once daily and such advantages are not predictable from the above-mentioned prior art.

The present invention will now be illustrated in more detail as hereunder.

Ramosetron and pharmaceutically acceptable salts thereof are easily available by a producing process mentioned in EP-A-381422 or by a method similar thereto.

With regard to the pharmaceutically acceptable salt of ramosetron, its specific examples are a salt with mineral acid such as hydrochloric acid, sulfuric acid, phosphoric acid and hydrobromic acid; a salt with organic acid such as acetic acid, oxalic acid, citric acid, maleic acid, malic acid, fumaric acid, tartaric acid and methanesulfonic acid; and a salt with acidic amino acid such as glutamic acid and aspartic acid. Among them, ramosetron hydrochloride which is commercially available is most preferred.

The drug of the present invention is able to be prepared as an oral solid preparation, an oral liquid preparation or an injection preparation according to conventional methods using organic or inorganic carrier, excipient and other additives suitable for oral or parenteral administration. Preferred ones are those which are able to be administered by a patient himself/herself and are convenient for preservation and carrying and, to be more specific, they are tablets, diluted powder, granules, fine granules, capsules, pills, etc.

In the solid preparation as such, an active substance is mixed with at least one inert diluent such as lactose, mannitol, glucose, microcrystalline cellulose, starch, polyvinylpyrrolidone and magnesium metasilicate aluminate. The composition may contain, by a conventional method, additives other than the inert diluent including a binder such as hydroxypropyl cellulose and hydroxypropyl methyl cellulose; a lubricant such as magnesium stearate, calcium stearate, polyethylene glycol, starch and talc; a disintegrating agent such as calcium cellulose glycolate; a stabilizer such as lactose; a dissolving aid such as glutamic acid and aspartic acid; a plasticizer such as Tween 80 and triacetin; and a coloring agent such as titanium oxide and iron sesquioxide. Tablets or pills may be coated, if necessary, with sugar coat or intragastrically soluble or enteric substance such as sucrose, gelatin, agar, pectin, hydroxypropyl cellulose and hydroxypropyl methyl cellulose.

In addition, like the commercially available "Nasea OD Tablets 0.1 mg", the preparation may be an intraorally disintegrating tablet. For example, the intraorally disintegrating tablet maybe prepared according to, for example, U.S. Pat. No. 5,466,464, U.S. Pat. No. 5,576,014, U.S. Pat. No. 6,589,554, WO 2003/009831, WO 2002/092058, etc.

Since the drug of the present invention contains ramosetron of a very low dose, preparations where a stabilization technique of temperature and humidity is applied are particularly preferred.

For example, when a specific compound having a carbonyl group is added, stabilization of ramosetron to temperature and humidity can be achieved. With regard to the specific compound having a carbonyl group, its specific examples are aliphatic carboxylic acid (to be more specific, saturated or unsaturated and linear or branched aliphatic mono-, di- or tri-carboxylic acid or, particularly, aliphatic carboxylic acid having 3 to 36 carbons) or ester thereof, hydroxycarboxylic acid (to be more specific, saturated or unsaturated and linear or branched aliphatic hydroxymono-, di- or tricarboxylic acid or, particularly, hydroxycarboxylic acid having 3 to 36 carbons) or ester thereof, acidic amino acid, enolic acid, aromatic carboxyl compound (to be more specific, aromatic mono-, di- or tri-carboxylic acid which may be substituted with alkyl group or hydroxyl group having 1 to 4 carbon(s) or, particularly, aromatic carboxylic acid having 7 to 20 carbons) or ester thereof and a macromolecular substance having a carboxyl group and those compounds may be appropriately used either solely or jointly by combining two or more thereof.

Particularly with regard to the specific compound having a carbonyl group, preferred ones are a hydroxycarboxylic acid or ester thereof, a macromolecular compound having a carboxyl group, an aromatic carboxyl compound or ester thereof and an enolic acid; particularly preferred ones are a hydroxycarboxylic acid or ester thereof, a macromolecular substance having a carboxyl group and an aromatic carboxyl compound or ester thereof; and more preferred ones are a hydroxycarboxylic acid or ester thereof and a macromolecular substance having a carboxyl group.

With regard to an aliphatic carboxylic acid, preferred ones are maleic acid, malonic acid, succinic acid and fumaric acid. As the hydroxycarboxylic acid, preferred ones are tartaric acid, malic acid and citric acid and more preferred ones are tartaric acid and citric acid. As the acidic amino acid, preferred ones are glutamic acid and aspartic acid. As the aromatic carboxyl compound, preferred ones are phthalic acid and propyl gallate and more preferred one is propyl gallate. With regard to a macromolecular substance having a carboxyl group, preferred ones are carboxymethyl cellulose and alginic acid and more preferred one is carboxymethyl cellulose. As the enolic acid, preferred ones are ascorbic acid and erythorbic acid and more preferred one is ascorbic acid.

The above-mentioned carbonyl compound in a form of a hydrate and an anhydride having no water of crystallization such as citric acid hydrate and citric acid anhydride also has been found to achieve a stabilizing effect of the present invention and the invention covers all hydrates, anhydrides and mixtures thereof. With regard to degree of polymerization, molecular weight, etc. of the macromolecular substance, although there is no particular limitation therefor, but a weight-average molecular weight of about 110,000 or about 200,000 is particularly preferred for carboxymethyl cellulose and alginic acid, respectively.

With regard to a compounding amount of a compound for the stabilization of ramosetron or a pharmaceutically acceptable salt thereof, there is no particular limitation so far as it is an amount for achieving the stabilization. It is, for example, 0.01 to 90% by weight, preferably 0.01 to 50% by weight or, more preferably and when its manufacture is also taken into consideration, 0.1 to 10% in the formulation.

Administering amount of ramosetron or a pharmaceutically acceptable salt thereof may be appropriately decided for each case by taking age, race, sex, etc. of the subject to be administered into consideration. In the case of ordinary oral administration of ramosetron hydrochloride, it is about 0.001 to 0.05 mg per day and, most preferably, 0.002 to 0.02 mg per day for an adult and that is orally administered after a meal once daily.

As discussed above, for certain human patient populations which may include Americans and Europeans for treatment of irritable bowel syndrome including diarrhea-predominant irritable bowel syndrome or to improve diarrhea symptom of irritable bowel syndrome, an optimum daily dose of ramosetron (amounts based on free base form) may be within a range of from 0.0025 mg to 0.05 mg, or more suitably a daily dose within a range of from 0.0025 mg to 0.02 mg or equivalent molar amounts of a pharmaceutically acceptable salt of ramosetron.

As would be understood, references herein to daily dosage amounts of ramosetron or pharmaceutically acceptable thereof designate the total amount of ramosetron or pharmaceutically acceptable salt thereof administered within a 24 hour period, where the total amount may be administered in a single administration (i.e., single daily dose) or multiple administrations (i.e., two or more dosages administered during the 24 hour period where the aggregate amount of the multiple dosages are within the daily dosage amount ranges disclosed herein). As discussed above, a single daily administration may be suitable in at least some protocols.

Therapeutic methods of the invention also may include a step of identifying a subject that is need for treatment for irritable bowel syndrome such as non-constipated irritable bowel syndrome which may include diarrhea-predominant irritable bowel syndrome and alternating constipation/diarrhea irritable bowel syndrome and/or to relieve or otherwise improve diarrhea symptoms of irritable bowel syndrome. The identification suitably can be in the judgment of a patient or a health professional and can be subjective (e.g., opinion) or objective (e.g., measurable by a test or diagnostic method).

A variety of therapeutic regimes may be utilized. For instance, a patient may be treated episodically, e.g. upon experiencing an acute attack of irritable bowel syndrome such as non-constipated irritable bowel syndrome and alternating constipation/diarrhea irritable bowel syndrome, ramosetron or a pharmaceutically acceptable salt thereof may be administered in a daily dosage amount as disclosed herein for a period sufficient to alleviate irritable bowel syndrome symptoms such as administration of ramosetron or a pharmaceutically acceptable salt thereof in daily dosage amounts as disclosed herein each day for up to 7 days, 14 days, 21 days, 28 days, 6 weeks, 8 weeks, 12 weeks, 16 weeks or more and then administration terminated until the patient again experiences the onset of irritable bowel syndrome symptoms. Alternatively, a patient may be maintained on a continuous or more prolonged therapy, e.g. an indefinite or prolonged administration (e.g. at least 6, 9, 12 or 15 months) of ramosetron or a pharmaceutically acceptable salt thereof in a daily dosage amount as disclosed herein each day as a prophylactic therapy to avoid or minimize the onset of irritable bowel syndrome symptoms. Other treatment protocols also may be utilized.

BEST MODE FOR CARRYING OUT THE INVENTION

The present invention will now be illustrated in more detail by way of the following Examples and Test Examples although the present invention is not limited by those Examples, etc.

EXAMPLE 1

| | |
|---|---|
| Ramosetron hydrochloride | 0.02 part |
| Lactose | 86 parts |
| Hydroxypropyl cellulose | 3 parts |
| Tartaric acid | 1 part |
| Yellow iron sesquioxide | 0.2 part |
| Titanium oxide | 10 parts |
| Light silicic acid anhydride | 0.3 part |

Hydroxypropyl cellulose (3 parts), 0.02 part of ramosetron hydrochloride and 1 part of tartaric acid were dissolved in 35 parts of water with stirring using a magnetic stirrer and kneaded with 10 parts of titanium oxide and 0.2 part of yellow iron sesquioxide using a grinding machine, and a spraying liquid (hydroxypropyl cellulose concentration: 8% by weight) was prepared. After that, 86 parts of lactose were charged in a fluid layer granulator (Flow Coater; manufactured by Freund) and the above spraying liquid was sprayed at a spraying rate of 5 g/minute to conduct a fluid granulation. The granules were dried for 5 minutes at an intake air temperature of 40° C. and then mixed with 0.3 part of light silicic acid anhydride to give a diluted powder preparation.

EXAMPLE 2

| | |
|---|---|
| Ramosetron hydrochloride | 0.0008 part |
| Mannitol | 89 parts |

-continued

| | |
|---|---|
| Citric acid anhydride | 0.1 part |
| Maltose | 10 part |
| Red iron sesquioxide | 1 part |
| Magnesium stearate | 1 part |

Maltose (10 parts), 0.0008 part of ramosetron hydrochloride, 0.1 part of citric acid anhydride and 1 part of red iron sesquioxide were suspended in 67 parts of water with stirring using a magnetic stirrer to prepare a spraying liquid (concentration: 15% by weight). After that, 89 parts of mannitol were charged in a fluidized bed granulator (Flow Coater; manufactured by Freund) and the above spraying liquid was sprayed at a spraying rate of 10 g/minute to conduct a fluid granulation. After the granulation, the granules were dried for 5 minutes at an intake air temperature of 40° C. and then mixed with 1 part of magnesium stearate. The mixed powder was made into tablets using a rotary tableting machine at the rate of 120 mg per tablet to give tablets having about 1 kp of initial hardness. They were preserved for 18 hours at a relative humidity of 75% and then preserved for 4 hours at a relative humidity of 40% to give intraorally disintegrating tablets.

EXAMPLE 3

The same manufacturing method as in Example 2 was conducted except that the adding amount of citric acid anhydride was changed to 0.2 part to give intraorally disintegrating tablets.

EXAMPLE 4

The same manufacturing method as in Example 2 was conducted except that the adding amount of citric acid anhydride was changed to 0.5 part to give intraorally disintegrating tablets.

EXAMPLE 5

| | |
|---|---|
| Ramosetron hydrochloride | 0.0008 part |
| Mannitol | 89 parts |
| Ascorbic acid | 0.2 part |
| Maltose | 10 parts |
| Red iron sesquioxide | 1 part |
| Magnesium stearate | 1 part |

Maltose (10 parts), 0.0008 part of ramosetron hydrochloride, 0.2 part of ascorbic acid and 1 part of red iron sesquioxide were suspended in 67 parts of water with stirring using a magnetic stirrer and a spraying liquid (concentration: 15% by weight) was prepared. After that, 89 parts of mannitol were charged in a fluidized bed granulator (Flow Coater; manufactured by Freund) and the above spraying liquid was sprayed at a spraying rate of 10 g/minute to conduct a fluid granulation. After the granulation, the granules were dried for 5 minutes at an intake air temperature of 40° C. and then mixed with 1 part of magnesium stearate. The mixed powder was made into tablets using a rotary tableting machine at the rate of 120 mg per tablet to give tablets having about 1 kp of initial hardness. They were preserved at 25° C. for 18 hours at a relative humidity of 75% and then preserved at 30° C. for 4 hours at a relative humidity of 40% to give intraorally disintegrating tablets.

EXAMPLE 6

The same manufacturing method as in Example 5 was conducted except that the adding amount of ascorbic acid was changed to 0.5 part to give intraorally disintegrating tablets.

EXAMPLE 7

| | |
|---|---|
| Ramosetron hydrochloride | 0.0008 part |
| Mannitol | 88 parts |
| Maltose | 10 parts |
| Yellow iron sesquioxide | 1 part |
| Citric acid anhydride | 0.2 part |
| Magnesium stearate | 1 part |

Maltose (10 parts), 0.0008 part of ramosetron hydrochloride, 1 part of red iron sesquioxide and 0.2 part of citric acid anhydride were suspended in 67 parts of water with stirring using a magnetic stirrer and a spraying liquid (concentration: 15% by weight) was prepared. After that, 88 parts of mannitol were charged in a fluidized bed granulator (Flow Coater; manufactured by Freund) and the above spraying liquid was sprayed at an intake air temperature of 50° C., a spraying rate of 10 g/minute and a cycle of spray/dry/shaking of 15 seconds/15 seconds/10 seconds to conduct a fluid granulation. After the granulation, the granules were dried for 5 minutes at an intake air temperature of 40° C. and then mixed with 1 part of magnesium stearate. The mixed powder was made into tablets using a rotary tableting machine at the rate of 120 mg per tablet to give tablets having about 1 kp of initial hardness. They were preserved at 25° C. for 18 hours at a relative humidity of 75% and then preserved at 30° C. for 4 hours at a relative humidity of 40% to give intraorally disintegrating tablets.

EXAMPLE 8

| | |
|---|---|
| Ramosetron hydrochloride | 0.01 part |
| Avicel | 86 parts |
| Low substituted hydroxypropyl cellulose | 10 parts |
| Citric acid anhydride | 0.5 part |
| Hydroxypropyl cellulose | 3 parts |
| Magnesium stearate | 0.5 part |

Hydroxypropyl cellulose (3 parts), 0.5 part of citric acid anhydride and 0.01 part of ramosetron hydrochloride were dissolved in 27 parts of water with stirring using a magnetic stirrer to prepare a spraying liquid (concentration of hydroxypropyl cellulose: 10% by weight). After that, 86 parts of Avicel and 10 parts of low-substituted hydroxypropyl cellulose were charged in a fluidized bed granulator (trade name: GPCG-5 manufactured by Powlex) and the above spraying liquid was sprayed at a spraying rate of 100 g/minute to conduct a fluid granulation. After the granulation, the granules were dried at 40° C. for 5 minutes and then mixed with 0.5 g of magnesium stearate. The mixed powder was made into tablets using a rotary tableting machine at the rate of 100 mg per tablet to give tablets.

EXAMPLE 9

| Ramosetron hydrochloride | 0.1 part |
|---|---|
| Lactose | 77 parts |
| Corn starch | 19 parts |
| Carboxymethyl cellulose (CMC) | 5 parts |
| Hydroxypropyl cellulose | 3 parts |
| Magnesium stearate | 0.3 part |

Hydroxypropyl cellulose (3 parts) and 0.1 part of ramosetron hydrochloride were dissolved in 35 parts of water with stirring using a magnetic stirrer to prepare a spraying liquid (concentration of hydroxypropyl cellulose: 8% by weight). After that, 77 parts of lactose, 19 parts of corn starch and 5 parts of CMC were charged in a fluidized bed granulator (trade name: Flow Coater manufactured by Freund) and the above spraying liquid was sprayed at a spraying rate of 10 g/minute to conduct a fluid granulation. After the granulation, the granules were dried at 5 minutes at an intake air temperature of 40° C. and then mixed with 0.3 parts of magnesium stearate. The mixed powder was made into tablets using a rotary tableting machine at the rate of 120 mg per tablet to give tablets.

EXAMPLE 10

| Ramosetron hydrochloride | 0.0008 part |
|---|---|
| Mannitol | 89 parts |
| Propyl gallate | 5 parts |
| Maltose | 10 parts |
| Magnesium stearate | 1 part |

Maltose (10 parts), 0.0008 part of ramosetron hydrochloride and 5 parts of propyl gallate were dissolved in 67 parts of water with stirring using a magnetic stirrer to prepare a spraying liquid (concentration: 15% by weight). After that, 89 parts of mannitol were charged in a fluidized bed granulator (Flow Coater manufactured by Freund) and the above spraying liquid was sprayed to conduct a fluid granulation. After the granulation, the granules were dried at 5 minutes at an intake air temperature of 40° C. and then mixed with 1 part of magnesium stearate. The mixed powder was made into tablets using a rotary tableting machine at the rate of 120 mg per tablet to give tablets.

TEST EXAMPLE 1

Clinical study with patients suffering from diarrhea-predominant irritable bowel syndrome Clinical study was carried out under the following condition using male and female patients suffering from diarrhea-predominant irritable bowel syndrome (IBS) as subjects.

Subjects: Patients suffering from diarrhea-predominant IBS in accordance with the Rome II Diagnosis Criteria (D. A. Drossman, et al., pages 351 to 432, ROME II: The functional Gastrointestinal Disorders, Second Edition, Degnon Associates, McLean, 2000).

Case Number: 418 cases

Test drugs and Administration Methods: Placebo and ramosetron hydrochloride were orally administered for 12 weeks at 0.005 mg or 0.01 mg once daily.

Test Periods: Observation period for one week and treating period for 12 weeks

Observed Items:

1. Main Evaluated Items (1) Global Assessment of Relief of Overall IBS Symptoms (Evaluation by the Subjects)

After transition to the treating period, the starting date for administration of the test drug was defined as the first day. Every week, global assessment of relief of overall IBS symptoms was evaluated taking all symptoms by IBS of the subjects into consideration, comparing with their state in the observation period, and this evaluation was recorded in a patient diary. Incidentally, scores for the global assessment of relief of overall IBS symptoms were as follows.

0=completely relieved
1=considerably relieved
2=somewhat relieved
3=unchanged
4=worsened The subjects where the score was 0 or 1 for two weeks or more during the four weeks were made monthly responders and the monthly responder rate per month was calculated separately for each group of 0.005 mg and 0.01 mg of placebo and ramosetron hydrochloride.

2. Subsidiary Evaluation Items (1) Global Assessment of Relief of Abdominal Discomfort/Pain (Evaluation by the Subjects)

After transition to the treating period, the starting date for administration of the test drug was defined as the first day. Every week, global assessment of relief of abdominal discomfort/pain by the test drug was evaluated with the state in the observation period and was recorded in a patient diary. Incidentally, scores for the global assessment of relief of abdominal discomfort/pain were as follows.

0=completely relieved
1=considerably relieved
2=somewhat relieved
3=unchanged
4=worsened (2) Global Assessment of Improvement of Abnormal Bowel Habits (Evaluation by the Subjects)

After transition to the treating period, the starting date for administration of the test drug was defined as the first day. Every week, global assessment of improvement of abnormal bowel habits was evaluated comparing with the state in the observation period, and was recorded in a patient diary. Incidentally, scores for the global assessment of improvement of abnormal bowel habits were as follows.

0=completely relieved
1=considerably relieved
2=somewhat relieved
3=unchanged
4=worsened (3) Severity of Abdominal Discomfort/Pain During the periods of clinical study (both observation period and treating period), the subjects evaluated the severity of abdominal discomfort/pain for each day and wrote in a patient diary. Scores for the severity of abdominal discomfort/pain were as follows.

0=none
1=mild
2=moderate
3=severe
4=intolerable (4) Stool Form (Appearance)

During the periods of clinical study, the subjects wrote the stool form (appearance) for each day using a score (type) of Bristol's stool form scale in a patient diary. When there were plural defecations within a day or when different stool forms (appearances) were noted in one defecation, only one form (appearance) which was the most representative one on that day (or for which the subject felt most troublesome) was written.

(5) Frequency of Bowel Movements

During the periods of clinical study, the subjects wrote the frequency of bowel movements for each day in a patient diary.

(6) Urgency

During the periods of clinical study, the subjects wrote whether there was urgency for each day in a patient diary.

(7) Feeling of Incomplete Bowel Movement

During the periods of clinical study, the subjects wrote whether there was feeling of incomplete bowel movement for each day in a patient diary.

With regard to (1) to (3) for the subsidiary evaluation items, they were also subjected to calculations of monthly responder rate the same as those for the main evaluation items.

Results:

With regard to the final monthly responder rate in the global assessment of relief of overall IBS symptoms, it was 26.9% in a placebo group. On the other hand, in the groups of 0.005 mg and 0.01 mg of ramosetron hydrochloride, the monthly responder rates were 42.6% and 43.0%, respectively and were more than 15% than the responder rate in the placebo group. The p values for the groups of 0.005 mg and 0.01 mg to the placebo group were 0.0273 and 0.0264, respectively. With regard to the difference in the responder rates between the placebo group and the ramosetron group for 0.005 mg and 0.01 mg, no difference was noted between male and female patients.

With regard to the final monthly responder rates in the global assessment of relief of abdominal discomfort/pain and in the global assessment of relief of abnormal bowel habits, the ramosetron hydrochloride group of 0.005 mg and 0.01 mg was also better than the placebo group to an extent of more than 10%.

From the above, the therapeutic effect of 0.005 mg and 0.01 mg of ramosetron hydrochloride to patients suffering from diarrhea-predominant irritable bowel syndrome was confirmed. It was also confirmed that, unlike alosetron disclosed in WO 99/17755, ramosetron hydrochloride was effective for both males and females and that, unlike the drug disclosed in WO 2002/007713, it was effective by administration once daily.

INDUSTRIAL APPLICABILITY

In accordance with the present invention, there can be provided an excellent agent for the treatment of irritable bowel syndrome including non-constipated irritable bowel syndrome such as diarrhea-predominant irritable bowel syndrome and alternating constipation/diarrhea irritable bowel syndrome or an agent for improvement of irritable bowel syndrome being effective for both males and females.

All documents mentioned herein are incorporated herein by reference.

The invention has been described in detail with reference to preferred embodiments thereof. However, it will be appreciated that those skilled in the art, upon consideration of this disclosure, may make modifications and improvements within the scope and spirit of the invention.

The invention claimed is:

1. A method for treating an adult human patient suffering from irritable bowel syndrome, comprising:

administering daily to the adult human patient 0.002 to 0.02 mg of ramosetron hydrochloride or an equivalent molar amount of ramosetron or other pharmaceutically acceptable salt thereof.

2. The method of claim 1 wherein 0.005 to 0.01 mg of ramosetron hydrochloride or an equivalent molar amount of ramosetron or other pharmaceutically acceptable salt is administered to the patient daily.

3. The method of claim 1 wherein the patient is suffering from non-constipated irritable bowel syndrome.

4. The method of claim 1 wherein the patient is suffering from diarrhea-predominant irritable bowel syndrome.

5. The method of claim 1 wherein the patient is suffering from alternating constipation/diarrhea irritable bowel syndrome.

6. The method of any one of claims 1 and 2 though 5 wherein the patient is an adult human male.

7. The method of claim 6 wherein ramosetron in free base form is administered to the patient.

8. The method of any one of claims 1 and 2 through 5 wherein the patient is an adult human female.

9. The method of claim 8 wherein ramosetron in free base form is administered to the patient.

10. The method of any one of claims 1 and 2 through 5 wherein ramosetron hydrochloride is administered to the patient.

11. The method of any one of claims 1 and 2 through 5 wherein ramosetron in free base form is administered to the patient.

12. A method for treating diarrhea symptom in an adult human patient suffering from irritable bowel syndrome, comprising:

administering daily to the adult human patient 0.002 to 0.02 mg of ramosetron hydrochloride or an equivalent molar amount of ramosetron or other pharmaceutically acceptable salt thereof.

13. The method of claim 12 wherein 0.005 to 0.01 mg of ramosetron hydrochloride or an equivalent molar amount of ramosetron or other pharmaceutically acceptable salt is administered to the patient daily.

14. The method of claim 12 wherein the patient is suffering from non-constipated irritable bowel syndrome.

15. The method of claim 12 wherein the patient is suffering from diarrhea-predominant irritable bowel syndrome.

16. The method of claim 12 wherein the patient is suffering from alternating constipation/diarrhea irritable bowel syndrome.

17. The method of any one of claims 12 and 13 though 16 wherein the patient is an adult human male.

18. The method of claim 17 wherein ramosetron in free base form is administered to the patient.

19. The method of any one of claims 12 and 13 through 16 wherein the patient is an adult human female.

20. The method of claim 19 wherein ramosetron in free base form is administered to the patient.

21. The method of any one of claims 12 and 13 through 16 wherein ramosetron hydrochloride is administered to the patient.

22. The method of any one of claims 12 and 13 through 16 wherein ramosetron in free base form is administered to the patient.

23. A method for treating an adult human patient suffering from irritable bowel syndrome comprising administering daily to the adult patient 0.0025 to 0.02 mg of ramosetron or an equivalent molar amount of a pharmaceutically acceptable salt of ramosetron.

24. A method for treating diarrhea symptom in an adult human patient suffering from irritable bowel syndrome comprising administering daily to the adult human patient 0.0025 to 0.02 mg of ramosetron or an equivalent molar amount of a pharmaceutically acceptable salt of ramosetron.

* * * * *